US012773284B2

(12) United States Patent
Junio et al.

(10) Patent No.: US 12,773,284 B2
(45) Date of Patent: Oct. 27, 2026

(54) SAFETY MECHANISM FOR ROBOTIC BONE CUTTING

(71) Applicant: Mazor Robotics Ltd., Caesarea (IL)

(72) Inventors: Dany Junio, Brookline, MA (US); Aviv Ellman, Kfar Sava (IL); Eli Zehavi, Tel Aviv (IL); Moshe Shoham, Hoshaya (IL); Yonatan Ushpizin, Glil Yam (IL); Ido Zucker, Tel Aviv (IL); Elad Ratzabi, Bitan Aharon (IL); Gillan Grimberg, Ramat Gan (IL); Nir Ofer, Tel Aviv-Jaffa (IL); Yair Schwartz, Herzliyya (IL); Nimrod Dori, Atlit (IL)

(73) Assignee: Mazor Robotics Ltd., Caesarea (IL)

( * ) Notice: Subject to any disclaimer, the term of this patent is extended or adjusted under 35 U.S.C. 154(b) by 0 days.

(21) Appl. No.: 18/754,066

(22) Filed: Jun. 25, 2024

(65) Prior Publication Data

US 2024/0341876 A1 Oct. 17, 2024

Related U.S. Application Data

(62) Division of application No. 17/569,957, filed on Jan. 6, 2022, now Pat. No. 12,048,497.

(Continued)

(51) Int. Cl.
*A61B 34/30* (2016.01)
*A61B 17/00* (2006.01)

(Continued)

(52) U.S. Cl.
CPC .............. *A61B 34/30* (2016.02); *A61B 17/17* (2013.01); *G16H 20/40* (2018.01); *G16H 40/63* (2018.01);

(Continued)

(58) Field of Classification Search
CPC .............. A61B 17/17; A61B 2034/107; A61B 2090/062; A61B 2090/064; A61B 17/1757
See application file for complete search history.

(56) References Cited

U.S. PATENT DOCUMENTS 12,048,497 B2 7/2024 Junio et al.
2005/0116673 A1 6/2005 Carl et al.

(Continued)

FOREIGN PATENT DOCUMENTS

WO WO 2019/215745 11/2019

OTHER PUBLICATIONS

Hu et al. "Use of an ultrasonic osteotome device in spine surgery: experience from the first 128 patients," European Spine Journal, 2013, vol. 22, pp. 2845-2849.

(Continued)

*Primary Examiner* — Kevin T Truong
*Assistant Examiner* — Diana Jones
(74) *Attorney, Agent, or Firm* — Sheridan Ross PC

(57) ABSTRACT

Methods and systems for providing a safety mechanism for a robotically controlled surgical tool. Embodiments of the methods use sensors to detect parameters that vary by the tissue traversed by a surgical tool. The sensors detect signals arising from the interaction of the surgical tool with the tissue and provide this information to a robotic controller. For example, during drilling, the sensors may measure power, vibration, sound frequency, mechanical load, electrical impedance, and distance traversed according to preoperative measurements on a three-dimensional image set used for planning the tool trajectory. By comparing the detected output with that expected for the tool position based on the planned trajectory, identified discrepancies in output would indicate that the tool has veered from the planned (Continued)

trajectory. The robotic controller may then alter the tool trajectory, change the speed of the tool, or discontinue power to the tool, thereby preventing damage to underlying tissue.

6 Claims, 7 Drawing Sheets

Related U.S. Application Data

(60) Provisional application No. 63/136,010, filed on Jan. 11, 2021.

(51) Int. Cl.

| | |
|---|---|
| ***A61B 17/17*** | (2006.01) |
| ***A61B 34/10*** | (2016.01) |
| ***A61B 90/00*** | (2016.01) |
| ***G16H 20/40*** | (2018.01) |
| ***G16H 40/63*** | (2018.01) |

(52) U.S. Cl.

CPC ... *A61B 2017/0003* (2013.01); *A61B 17/1757* (2013.01); *A61B 2034/107* (2016.02); *A61B 2090/062* (2016.02); *A61B 2090/064* (2016.02); *A61B 2562/0204* (2013.01)

(56) References Cited

U.S. PATENT DOCUMENTS

| | | | | |
|---|---|---|---|---|
| 2011/0015649 | A1 | 1/2011 | Anvari et al. | |
| 2014/0276849 | A1 | 9/2014 | Voic | |
| 2018/0042684 | A1 | 2/2018 | Kostrzewski et al. | |
| 2018/0085172 | A1 | 3/2018 | Bell et al. | |
| 2018/0242985 | A1 | 8/2018 | Viperman et al. | |
| 2018/0289432 | A1 | 10/2018 | Kostrzewski et al. | |
| 2019/0090966 | A1 | 3/2019 | Kang et al. | |
| 2019/0201120 | A1 | 7/2019 | Shelton, IV et al. | |
| 2019/0336220 | A1 | 11/2019 | Hladio et al. | |
| 2020/0289133 | A1 | 9/2020 | Elbanna et al. | |
| 2020/0337782 | A1 | 10/2020 | Glassman et al. | |
| 2021/0282862 | A1 * | 9/2021 | Bourlion ................ | A61B 34/10 |

OTHER PUBLICATIONS

Parsian et al. "Sound analysis in Drilling, Frequency and Time Domains," Procedia CIRP, 2017, vol. 58, pp. 411-415.

International Search Report and Written Opinion for International (PCT) Patent Application No. PCT/IL2022/050029, dated May 16, 2022, 18 pages.

Official Action for U.S. Appl. No. 17/569,957, dated Nov. 22, 2023, 8 pages Restriction Requirement.

Official Action for U.S. Appl. No. 17/569,957, dated Jan. 9, 2024, 10 pages.

Notice of Allowance for U.S. Appl. No. 17/569,957, dated Apr. 18, 2024, 9 pages.

Praamsma et al. "Drilling sounds are used by surgeons and intermediate residents, but not novice orthopedic trainees, to guide drilling motions," Journal Canadien De Chirurgie, Dec. 2008, vol. 51, No. 6, pp. 442-446.

Shao et al. "Drilling Condition Identification Based on Sound Pressure Signal in Anterior Cervical Discectomy Surgery," Medical Science Monitor, Sep. 2019, pp. 6574-6580.

Official Action for European Patent Application No. 22703721.5, dated Oct. 30, 2025, 12 pages.

Official Action with English Translation for China Patent Application No. 202280009402.0, dated Mar. 23, 2026, 30 pages.

* cited by examiner

SAFETY MECHANISM FOR ROBOTIC BONE CUTTING

CROSS REFERENCE TO RELATED APPLICATIONS

This application is a division of U.S. patent application Ser. No. 17/569,957, filed on Jan. 6, 2022, and entitled "Safety Mechanism for Robotic Bone Cutting", which claims the benefit of U.S. Provisional Application No. 63/136,010, filed on Jan. 11, 2021, and entitled "Safety Mechanism for Robotic Bone Cutting", both of which applications are incorporated herein by reference in their entireties.

FIELD

The present disclosure describes technology related to the field of robotic orthopedic surgery, especially to safety mechanisms while robotically cutting or drilling bone.

BACKGROUND

In orthopedic procedures performed either manually or robotically, use is made of cutting or drilling tools, whether conventional tools or ultrasonic blades. Ultrasonic powered tools having become the tool of choice for many orthopedic procedures, especially for delicate work in sensitive regions, such as on the spine. One of the important challenges in such procedures, is the need for multiple safety layers applied to the system to prevent damage to underlying or surrounding tissue. This requirement is important in robotically executed procedures, since reliance on the expected position of anatomic features, based on the initial registration of the intraoperative robot co-ordinate system with preoperative three-dimensional images, may be compromised should tissues undergo unexpected positional changes during the operation. For example, soft tissues may shift unexpectedly, or be compressed more than anticipated, when the cutting tool is operating using large forces in bone adjacent to that tissue, such that forces used when cutting or sawing bone tissue, should be avoided as much as possible. However, such care cannot be maintained in all situations, and the problem then arises of how to avoid compromising the system registration because of soft tissue motion. Furthermore, the danger of damage to regions surrounding the bone tissue, when that bone tissue is being cut or otherwise operated on, should be minimized Reference is made to the following documents, which describe features of such bone cutting procedures:

- "Use of an ultrasonic osteotome device in spine surgery: experience from the first 128 patients", Hu X, Ohnmeiss D D, and Lieberman I H. Eur Spine J. 2013 December; 22 (12): 2845-2849.
- "Sound analysis in drilling, frequency, and time domains"; by Parsian A, Magnevall M, Beno T, and Eynian M. Procedia CIRP 58 (2017) 411-415.
- US 2014/0276849 to Voic D, for "Method for ultrasonic tissue excision with tissue selectivity", published Sep. 18, 2014, and assigned to Misonix, Inc.

The disclosures of each of the publications mentioned in this section and in other sections of the specification, are hereby incorporated by reference, each in its entirety.

SUMMARY

The present disclosure describes new exemplary systems for safety mechanisms to prevent collateral damage to tissues by a drill, milling tool, or saw cutting through bone. Implementations of the disclosed system utilize at least one of a number of sensors to give feedback to the system regarding the properties of the tissue through which the tool is traversing.

In a robotically controlled surgical procedure, a preoperative plan for execution by a surgical robotic system is generally based on a three-dimensional preoperative image set of the operative area. The planned trajectory of the surgical tool is calculated based on these images. Intraoperatively, the actual trajectory of the tool is accomplished by positioning the tool tip in accordance with the preoperative images, typically using a registration procedure as described below. In a spinal procedure, known measurements of the vertebral body, pedicle, and other anatomical features of interest can be used to provide information to the system or to the human operator regarding the position of the tool tip in three dimensions. This registration between the preoperative images of the operative region and the subject's intraoperative anatomy allows a determination of the progress of the tool, including, for example, the distance remaining until the edge of the saw or tip of the surgical tool reaches a position in which it would present a danger to the patient.

However, even though the procedure is performed according to a surgical plan based upon preoperative images to which is registered the robotically positioned tool tip, small shifts in the deeper tissues relative to the surface may introduce small but significant changes in the position of anatomical features relative to the actual position of the tool. In other words, the tissues through which the tool is passing, may not be those which the system calculates that they should be according to the original surgical plan, whether due to a lateral shift, or a shift in the depth at which the tissue is encountered. Even in those procedures where the surgical plan and tool trajectory are calculated on the basis of intraoperative CT images, which may reflect a more up-to-date position of the bones and surrounding tissues, there may still be motion of the bone and tissues occurring intraoperatively, because of the various operation procedures, and such motion may then lead to discrepancies between the actual tissue in which the tool is operating, and the tissues expected to be at that location, even according to an intraoperatively generated surgical plan.

Thus one of the challenges in automating robotic surgical procedures, especially procedures such as bone cutting, milling or drilling, is the need for reliable safety mechanisms to provide warning that the position of the surgical tool has changed relative to the tissue in which it is calculated to be operating, or that the tool is approaching or encroaching on a tissue in which it would be dangerous to operate. In particular, warning should be provided that the surgical tool has unexpectedly passed, or is about to pass, from bone tissue to surrounding soft tissue or organs. Additionally, passage from cortical bone to cancellous bone, or from cancellous bone to cortical bone, may also necessitate that a warning, or at least a notification, be provided to the operator. Furthermore, even when navigation tracking is being used to directly track the pose of the bone on which the tool is performing the operating procedure, such that motion of the bone may be taken into account, the possibility of the unintentional blocking of the visual line of sight of the optical tracking beam, may mandate an additional non-dependent protection layer for the safe performance of the procedure.

The present disclosure describes new exemplary safety mechanisms to reduce the likelihood of such errors. Such methods and systems are based on the use of sensors to detect parameters that change, as a function of the tissue in which the surgical tool is operating. Not only do different tissues have varied densities and properties, but the outer regions of some tissues, in particular, bony tissues, may have different properties from the inner regions. Thus, information collected by sensors should provide an indication of whether the surgical tool has already entered tissue in its planned path, having different properties from those expected for the planned path. In addition, the information should preferably also give an indication as to whether the surgical tool is approaching a tissue through which, according to the surgical plan, the tool is not intended to traverse, even before the tool reaches the boundary.

Information collected by the sensors may include at least some of:

(i) The sound emitted by the drilling or cutting process.
(ii) The electrical power drawn by the surgical tool, or by the robot.
(iii) The sound emitted by the tool motor during its progress.
(iv) The mechanical force which the tool experiences by the reaction of the surgical tool with a tissue, especially with bone, as it proceeds with its task.
(v) Mechanical vibrations which the tool undergoes as it proceeds through the bone.
(vi) The electrical impedance sensed between the surgical tool tip and the subject's body.

The above information collected by sensors can be used to assist in determining tissue properties in which the surgical tool is operating. The system may include a database storing the type and/or level of sensor responses anticipated for each of the relevant sensor devices, as the surgical tool passes through cortical bone, cancellous bone, and a variety of soft tissues. The system is configured to identify the position of the tool relative to the tissues through which it passes, based on registration with the preoperative images. Thus, the system can compare the actual sensor outputs generated, with the data stored in the database for the expected sensor output for the planned tool path, thereby providing information identifying the tissue in which the surgical tool is actually operating, and providing a warning if the tool has departed significantly from its intended trajectory. This departure can be established if the actually measured sensor output is not in agreement with the output expected from the interaction of the surgical tool with the tissue in which it is assumed that the surgical tool is located, as determined by the known position of the surgical tool in its robotic trajectory. This lack of agreement can be manifested in a number of ways, most commonly by the level or magnitude of the measured effect, but also by other effects, such as by the frequency of the effect measured, or by any other measurement discordance which implies a lack of matching or a difference between the expected and the actual measured effect.

Tissue properties not only differ between types of tissue, such as between bone and soft tissue, but may additionally differ based on other factors, such as the age of the person operated on. For example, the difference between the density of cortical bone and cancellous bone in an osteoporotic woman of age 80 is expected to be less than in a 30-year-old man. The system can advantageously use machine learning and big data to calculate the expected sensor responses for different positions within the patient, by analyzing data collected from a variety of sources. These sources may comprise at least some of the patient's clinical history, information collected from the pre-operative images and other imaging modalities such as a bone density scan, clinical and postoperative outcome data collected from other patients who have previously undergone similar surgical procedures. The actual sensor responses recorded during the operation are then compared with the expected responses to provide an indication of the tissue properties through which the tool is traveling.

Artificial intelligence may be employed intraoperatively to analyze specific patterns and behaviors of sensor outputs as different surgical tools traverse different tissues. The system can thus learn to identify when a tool traverses an unexpected anatomical structure, or even an anatomical structure at an unexpected position or depth from that indicated in the original surgical plan. Thus the presently disclosed methods provide for the application of artificial intelligence methods to analyze sensor output parameters related to tool movement that correlate with tool position, thereby providing a safety mechanism for robotic operation of the tool even without direct visual or sensory feedback on the tool location itself.

An additional or alternative way of using a database of expected sensor output values to give an indication of the tool transitioning between one tissue and another, is to configure the system to respond, should a sensor output value change by more than a predetermined amount, indicating a danger to the subject. The amount may be an absolute cutoff value, or a relative increase or decrease, or a change in the rate of increase or decrease, of the parameter measured by the sensor. A significant change in sensor output values signify that the tool has transitioned, or is transitioning, to a tissue having tissue properties different from that in which it was previously operating. This change may be acceptable if expected; however, if the detected tissue position of the tool is different from that calculated by the surgical plan for that point of the planned trajectory, it may trigger a warning or response from the system. A primary use of the safety mechanism is for monitoring and ensuring the position of the tool tip within a tissue in which the tool should be operating, and preventing unexpected exit from that tissue, such as bone, into an adjacent, damageable tissue.

Using the sensor outputs, the system may be able to provide information regarding the depth of tool penetration through the tissue. This situation exists when the sensor output provides a different output depending on the distance from the outer edge of the presently monitored tissue. Thus, should the surgical tool mistakenly advance towards the edge of a permitted area, beyond which it would impinge on an area where the tool is forbidden to operate, such as the spinal canal or soft tissue, advance warning of the approaching boundary should be provided to the surgeon or to the robotic controller.

Further to the basic aim of the system of avoiding a surgical tool unintendedly breaking out of a bone and damaging sensitive soft tissues, an additional advantage of the system is the use of sensor output to enable the utilization of more of the subject's bone depth than originally planned. One example would be, for example, enabling the insertion of pedicle screws to a greater depth. Besides, or in addition to, the sensors detecting an approach to a forbidden region, they may also be used to detect distance still remaining to a forbidden region, thereby allowing for further penetration of the drill into the bone and use of the full available expanse of the bone.

The drilling of a pedicle screw hole can be used as an example of the criticality and need of the presently disclosed systems. The vertebral pedicle is a narrow bridge of bone between the vertebral body and the spinous processes, and the margin of error for aligning the drill is narrow at this point, such that a small error may have serious results. Especially for a robotically performed procedure, the system needs to be configured with added layers of safety, beyond the instruction set supplied to the robot by the surgical plan based on preoperative three-dimensional images. Because the robot lacks the sensory feedback that a human operator would feel, additional safety mechanisms are necessary to prevent inadvertent damage to either the neural tissue within the spinal canal, the paraspinal muscles on the exterior of the vertebrae, or peripheral nerves and blood vessels.

If, or when the system senses that the saw, drill, or milling tool is close to impinging on a forbidden area, or that it is deviating more than a certain amount from the planned trajectory, the system may employ a number of options for averting tissue damage or for preventing the tool from entering a region where it is not allowed. The controller may either turn off power to the tool or slow down its speed; or it may change the trajectory of the tool via robotic control; or it may opt to turn off the robot so that the tool progress can be checked.

Current bone cutters or saws employ ultrasound vibration of the blade to enable cutting. Such tools have an inherent safety mechanism because of the differential cutting capacity in tissues having different densities. It is known that an ultrasound cutting blade is able to make initial contact with soft tissue without coupling the level of energy into the tissue that would result in cutting the tissue. Instead, the tool would rather simply deflect the soft tissue. This is in contrast to contact of the same blade at the same power with a hard tissue, which would result in a cutting action. However, more positive pressure on the soft tissue would generally result in damage thereto. Consequently, adding another layer of safety would be advantageous, since during the operation, anatomical features in the operative field may shift or slide relative to the surface level positions on which registration had been performed.

Implementations of the presently disclosed methods provide for the application of artificial intelligence methods to analyze parameters related to tool movement, that correlate with tool position, thereby providing a safety mechanism for robotic operation of the tool even without direct visual or sensory feedback on the tool location. In at least one exemplary implementation, operating parameters of the surgical tool itself may be used to identify, plan for, and/or resolve a safety issue. For example, the ratio between force applied to the surgical tool and torque of the surgical tool (e.g., while drilling through bone) may be indicative of a problem, for example, when the ratio is not within an expected range. In this case, historical data regarding the same ratio from other procedures may be used to help identify the problem(s) and/or possible solution(s).

There is thus provided in accordance with an exemplary implementation of the devices described in this disclosure, a robotic surgical system, comprising:

(a) a controller configured to control the position of a surgical tool according to a planned trajectory, the planned trajectory passing through different tissues, and (b) at least one sensor adapted to output a signal from the interaction of the surgical tool with a tissue on which the surgical tool is operating, wherein the controller is further configured to:

(i) determine an expected tissue corresponding to the known position of the surgical tool in the planned trajectory, (ii) from a dataset comprising tissue-specific sensor output signals, identify the expected signal output from at least one sensor, resulting from the interaction of the surgical tool with the expected tissue, (iii) compare the expected signal output from the at least one sensor with the measured signal output from the at least one sensor resulting from the interaction of the surgical tool with the tissue on which the surgical tool is operating, and (iv) if the measured signal output is not in agreement with the expected signal output from the expected tissue in which the surgical tool is operating, conclude that the surgical tool is not following its planned trajectory.

In the above described robotic surgical system, the at least one sensor may be adapted to sense any one of:

(i) a sound emitted by the surgical process, (ii) the electrical power drawn by the surgical tool or by the robot, (iii) a sound emitted by a motor of the surgical tool during its progress, (iv) the mechanical force experienced by the reaction of the surgical tool with the tissue, (v) mechanical vibrations which the surgical tool undergoes as it proceeds through the tissue, (vi) the electrical impedance of the tissue in which the tool is operating, and (vii) change in motor speed of the surgical tool, and (viii) change in motor torque of the surgical tool.

Furthermore, in such robotic surgical systems, if it is determined that the surgical tool is not following its planned trajectory, the controller may be configured to instruct the execution of at least one of:

(i) halting motion of the tool along the planned trajectory, (ii) reducing the advance speed of the surgical tool, (iii) reducing the machining ability of the surgical tool, (iv) turning off power to the surgical tool, and (v) issuing a warning to the operator of the system.

Additionally, in any of the above described robotic surgical systems, the surgical tool may be adapted to perform at least one of cutting, milling, drilling and sawing a bone tissue. Furthermore, the known position of the surgical tool may comprise the distance along a tool path of the planned trajectory. Moreover, the planned trajectory may include a procedure in a bone tissue, and a deviation from the planned trajectory may then comprise the passage of the surgical tool out of the bone tissue.

If, in any of the above described robotic surgical systems, it is determined that the surgical tool is not following its planned trajectory, the controller may be further configured to prevent the surgical tool from entering a tissue which is not in accordance with the planned trajectory. In such a case, the controller may be further adapted to use an output of at least one sensor to determine the depth remaining for the procedure within the bone tissue. The controller may then be further adapted to instruct the continuation of the procedure in the bone tissue to a depth deeper than that indicated by the planned trajectory, if the depth determined as remaining within the bone tissue is greater than that expected from the planned trajectory.

According to yet further implementations of the robotic surgical systems of this disclosure, the signal output expected from any of the at least one sensors may be adjusted to reflect at least one of: bone density, age, gender, skeletomuscular condition, osteoporosis measured by z-score, and any concomitant disease of the subject. Additionally, actions performed by the controller may comprise the controlled movement of a robotic arm holding the surgical tool. Furthermore, the dataset of tissue-specific sensor output signals may comprise anticipated values of sensor output signals generated by the passage of the surgical tool through any of cortical bone, cancellous bone, and different types of soft tissues.

There is further provided, according to another implementation described in this disclosure, a method for monitoring progress of a robotically directed surgical tool along a predetermined path through different tissues, the method comprising:

(i) determining from a known position of the surgical tool along the predetermined path, a tissue which the surgical tool is expected to be traversing,
(ii) detecting at least one sensor output arising from the interaction of the surgical tool with the tissue which it is traversing,
(iii) comparing the at least one sensor output with the expected sensor output from the interaction of the surgical tool with the tissue which the surgical tool is expected to be traversing, and
(iv) determining that the surgical tool is departing from the predetermined path if the comparison shows that the at least one sensor output is meaningfully different from the expected sensor output.

In such a method, the at least one sensor may detect at least one of:

(i) a sound emitted by the surgical process,
(ii) the electrical power drawn by the surgical tool or by the robot,
(iii) a sound emitted by a motor of the surgical tool during its progress,
(iv) the mechanical force which the surgical tool experiences by the reaction of the surgical tool with the tissue,
(v) mechanical vibrations which the surgical tool undergoes as it proceeds through the tissue, and
(vi) the electrical impedance of the tissue which the tool is traversing.

Furthermore, in either of those methods, if the surgical tool is found to be departing from the predetermined path, there is performed at least one of:

(i) halting motion of the tool along the planned trajectory,
(ii) reducing the advance speed of the surgical tool,
(iii) reducing the machining ability of the surgical tool,
(iv) turning off power to the surgical tool, and
(v) issuing a warning to the operator of the system.

In any of the above described methods, the predetermined path through different tissues may include a procedure in a bone tissue, and the departure from the predetermined path may comprise the passage of the surgical tool out of the bone tissue. The methods may further comprise the use of artificial intelligence to analyze whether the at least one sensor output is falling outside of a predetermined normal range from the expected sensor output. Furthermore, if it is determined that the tool is departing from the predetermined path, the method may instruct performing at least one of: disabling power to the tool, decreasing power to the tool, or changing a trajectory of the tool.

According to yet further implementations of the systems described in this application, there is provided a robotic surgical system, comprising:

(i) a controller configured to control movements of a robotically controlled surgical tool according to a surgical plan, and
(ii) at least one sensor, each of which is adapted to detect an output arising from the interaction of the tool with a tissue of a subject, and to transmit the detected tool-tissue interaction output to the controller, wherein if at least one of the tool-tissue interaction outputs departs by more than a predetermined normal range from the tool-tissue interaction output expected from the tissue with which the surgical tool is interacting according to a surgical plan, concluding that the surgical tool has departed from the surgical plan.

In such a system, the tool-tissue interaction output may comprise at least one of (i) a sound emitted by the surgical process,
(ii) the electrical power drawn by the surgical tool or by the robot,
(iii) a sound emitted by a motor of the surgical tool during its progress,
(iv) the mechanical force which the surgical tool experiences by the reaction of the surgical tool with the tissue, as it proceeds with its task,
(v) mechanical vibrations which the surgical tool undergoes as it proceeds through the tissue, and
(vi) the electrical impedance sensed between the surgical tool tip and a tissue of the subject, In any of the above described systems, the tool-tissue interaction outputs expected from the tissue with which the surgical tool is interacting may be obtained from a database of projected tool-tissue interaction outputs for a range of tissues and for a range of surgical tool conditions. Additionally, the at least one of the tool-tissue interaction outputs may comprise a plurality of tool-tissue interaction outputs matched with at least one tissue type. Furthermore, in these systems, the controller may be adapted to use a sound emitted by the surgical process in bone tissue to provide an indication of the depth within the bone tissue that the surgical tool is positioned. Moreover, if the sound emitted by the surgical process is undergoing an increase in pitch, the system may be configured to identify this as an indication that the surgical tool is approaching an end boundary of the bone tissue. In these systems, the sound detected by the at least one sensor may comprise either or both of the frequency and the volume arising from the interaction of the tool with a tissue of the subject.

According to further implementations of such systems, at least one of (i) the power drawn by a motor of the surgical tool,
(ii) the pitch of the sound waves generated by a motor of the surgical tool,
(iii) mechanical vibrations which the surgical tool undergoes as it proceeds through the tissue, and
(iv) a mechanical force which the surgical tool requires to traverse a tissue, may be used to provide an indication of at least one of the softness or the density of the tissue which the surgical tool is traversing.

Additionally, in any of these systems, the controller may be adapted to perform at least one of (i) terminating power to the tool, (ii) decreasing power to the tool, (iii) changing a trajectory of the tool, or (iv) issuing a warning to the system operator, should at least one tool-tissue interaction output depart by more than a predetermined limit from the output expected from the tissue which the tool is expected to be traversing according to the surgical plan.

A further exemplary embodiment described in this disclosure involves a safety system for executing a surgical procedure on a subject by a robotically controlled surgical tool, the system comprising:

(a) a controller configured to control movements of the robotically controlled surgical tool according to a planned trajectory, and (b) at least one sensor adapted to output a signal according to the interaction of the surgical tool with a tissue on which the surgical tool is operating, wherein the controller is further configured to:

(i) determine from the planned trajectory an anatomical feature in which the surgical tool is estimated to be operating, (ii) receive output signals transmitted by at least one sensor, and (iii) provide an indication that the surgical tool has departed from the planned trajectory if, at least one of:

(c) at least one sensor signal is outside of a predetermined range expected for a sensor signal as a result of the tool traversing the tissue on which the surgical tool is operating, (d) a pattern of behavior of sensor signals is received from at least one sensor differing by more than a predetermined degree from the pattern expected by the tool traversing the planned trajectory, or (e) each of at least two sensor signals being outside of a predetermined range within which each sensor signal is expected to be as a result of the tool traversing the planned trajectory.

A further implementation of the methods of this application is for a safety mechanism for a bone-machining tool under robotic control, comprising:

(i) using at least one sensor to detect a change in at least one quantifiable parameter as the bone-machining tool is moved by the robotic control, the at least one quantifiable parameter changing when the bone-machining tool is moved through bone as compared to a soft tissue adjacent to the bone, and (ii) sending an instruction to the robotic control to take action to provide protection to the soft tissue adjacent to the bone, based on the change in the at least one quantifiable parameter.

In the above described method, the action taken by the robotic control to protect the soft tissue adjacent to the bone may include at least one of:

(i) halting motion of the bone-machining tool, (ii) reducing the advance speed of the bone-machining tool, (iii) reducing the machining ability of the bone-machining tool, (iv) turning off power to the bone-machining tool, and (v) issuing a warning to an operator of a system using the bone-machining tool.

In this method, the quantifiable parameter may comprise at least one of:

(i) a sound emitted by the operation of the bone-machining tool, (ii) the electrical power drawn by the bone-machining tool, (iii) a sound emitted by a motor of the bone-machining tool during its motion, (iv) the mechanical force which the bone-machining tool experiences by its reaction with the bone or the adjacent tissue, (v) mechanical vibrations which the bone-machining tool undergoes as it is moved by the robotic control, and (vi) the electrical impedance of the tissue which the bone-machining tool is traversing.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

Definitions

Segmental tracking, in the context of this application, is the intraoperative use of real time imaging, such as ultrasound, to measure the position of a tool relative to tissue features.

Edge learning is the process of learning using the tool tip; intraoperatively, this is accomplished by touching different tissues and recording information from the tissue.

BRIEF DESCRIPTION OF THE DRAWINGS

The present invention will be understood and appreciated more fully from the following detailed description, taken in conjunction with the drawings in which.

DETAILED DESCRIPTION

Figure 1:
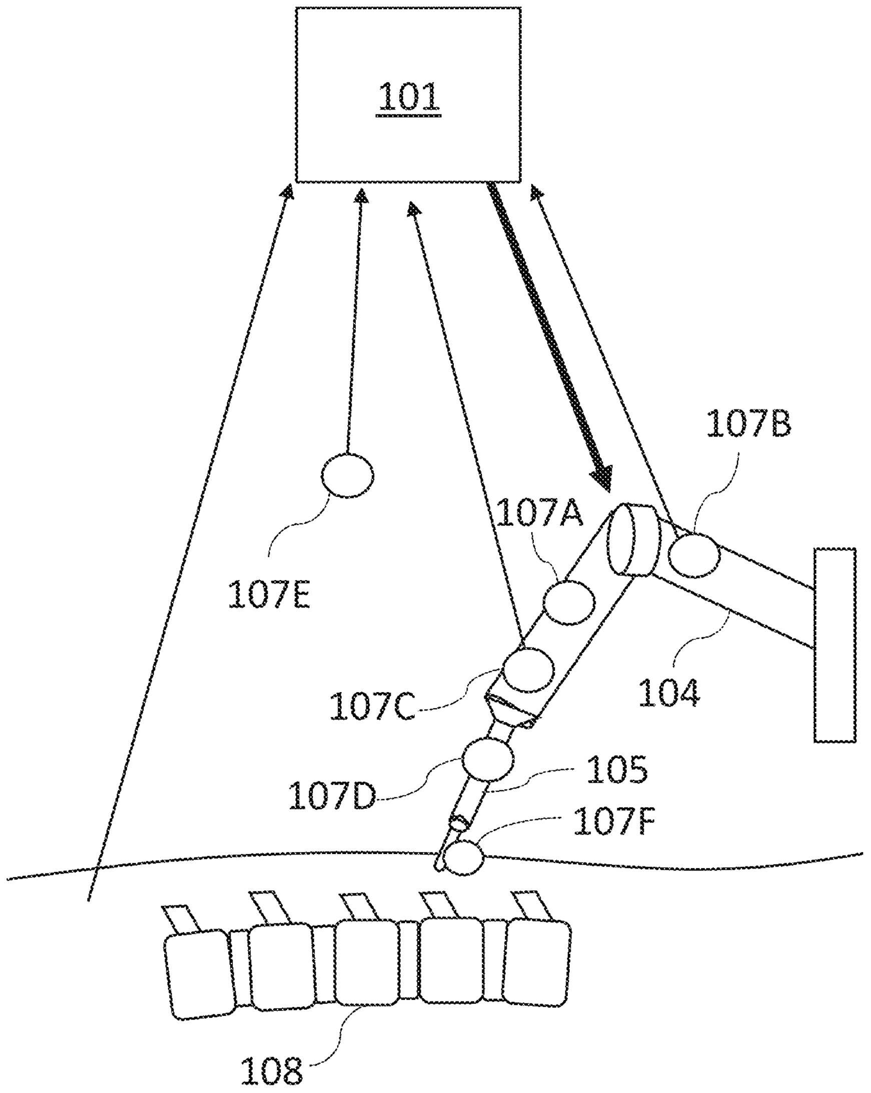
FIG. 1 shows an exemplary surgical robotic system using sensors for detecting the tissue type through which a surgical tool is passing.

Reference is now made to FIG. 1, which illustrates schematically an exemplary surgical robotic system with a controller 101, and at least one robotically controlled arm 104. The controller is typically supplied with, or calculates, a surgical plan for the patient, which may be based on information gathered from preoperative or intraoperative images. The co-ordinate system of the robot should be registered to the images used to generate the surgical plan, such that when the controller provides instructions to the robot 104, enabling it to carry out the surgical plan using one or more surgical tools 105, the projected location of the surgical tool tip 105 relative to the position of anatomical structures of the patient can be calculated by or is known to the controller.

In a typical implementation, the surgical tool 105 may be a saw, a drill, or a milling head, any of which may be conventional, or an ultrasonic cutting tool that can penetrate bony tissue. In the case of the exemplary procedure shown in FIG. 1, the surgical procedure illustrated is a spinal fusion operation, and the tool is a drill designed to form the hole for insertion of a pedicle screw into a vertebra 108. During operation of the system, the robotic arm 104, operated by the controller 101, moves the surgical tool 105 to carry out the steps of the procedure; in this exemplary case, drilling a hole from the posterior aspect of the vertebra into the pedicle.

In order to confirm that the surgical tool 105 is following the trajectory indicated by the surgical plan, as indicated by the coordinates registered by the controller, and in order to ensure that it is not approaching or entering unintended areas, a number of sensors 107A, 107B, 107C, 107D and 107E provide information to the controller 101 regarding the properties, which each sensor detects, of the tissue in which the surgical tool 105 is moving. For reasons of clarity of the drawing, FIG. 1 does not show all of the paths of sensor information to the controller.

From the properties of the tissues, the controller can ascertain whether the surgical tool 105 is approaching, or has already entered into, unintended areas, such as soft tissue. In one embodiment of the system, the responses of sensors 107A-E are used to determine whether the surgical tool is operating in the tissue which was expected by the trajectory as delineated by the surgical plan. If not, the controller 101 uses at least some of these sensor outputs to adjust the robotic actions, generally by halting the forward motion of the tool, or by halting the cutting action, and by providing a warning to the surgeon, as discussed further below.

For the example of operation on bone, the sensors may include any one of, or a combination of, the following:

(i) A sound sensor 107E adapted to collect data regarding the sound emitted by the surgical process itself, both frequency and intensity.

(ii) A power sensor 107B adapted to collect data regarding the amount of electrical power being consumed by the motor of the surgical tool.

(iii) A sensor 107C adapted to collect data regarding the frequency and intensity of the vibration emitted by the tool motor during its progress.

(iv) A force sensor 107D adapted to detect the mechanical force which the tool encounters as it proceeds through the bone.

(v) A mechanical vibration sensor 107A adapted to collect data regarding the mechanical vibrations which the tool emanates as it proceeds through the tissue.

(vi) An electrode 107F adapted to collect data regarding the electrical impedance of the tissue in the region of the tool tip, as sensed between the tool surgical tip and the subject's body.

(vii) A timer, a clock, or suitable sensor (not shown) that provides timing information for determining whether the time taken to make a particular cut with the surgical tool matches an expected amount of time taken for the cut or is within a threshold amount of time of an expected amount of time taken for the cut, where the expected amount of time taken may be based on historical information about how long a particular cut takes with the tool. This feature covers a use case where the time taken for a cut may be considered as standalone information or in addition to other information from other sensors. One embodiment may track the time taken for a cut vs planned time for the cut and/or account for the time factor for other measurements. If the time taken for a cut is outside of a threshold amount of time from the expected amount of time, then the system may issue a notification to the surgeon with information about the expected amount of time for the cut and the actual amount of time for the cut (e.g., information about the different between actual and expected amount of times).

The sensors all provide their output signals to the controller 101, whose processor analyzes the outputs and calculates any dissident data from that expected from the surgical plan trajectory and procedure. Should such a departure of the data from that expected be experienced, the robotic system should adjust the robotic action accordingly, and at the same time, issue a warning to the attending surgeon, who can then inspect the surgical situation to ensure that the robotic action is being corrected in a safe manner, or its progress aborted.

In FIG. 1, the relative position of each sensor has been shown schematically, though it is to be understood that each sensor will be located in a position where it can detect the particular parameter which it is intended to measure. Thus, for instance, the power sensor 107B may be situated in the system controller 101, rather than on the circuitry within the robot itself, and the tool mechanical vibration sensor 107A may preferably be located close to the tool holder.

Vibration sensor 107A is adapted to detect the mechanical vibration undergone by the drill or other surgical tool 105 as it travels through the tissue. Different materials will cause different vibrations, as the softness, density, and other tissue properties can cause the drill to vibrate differently in different materials.

Both the power used by the drill motor to insert the drill bit through harder or denser tissue, and the mechanical load or force required for this process, are considerably greater than would be needed to propel the drill bit through a softer or less dense tissue. Thus, power sensor 107B may be used to measure the amount of power drawn by the motor of the surgical tool 105, and force sensor 107D located in-line with the drill may be used to measure the force required to propel the drill through the tissue.

An indirect measurement of the power used by the drill can be obtained by the pitch of the sound waves generated by the drill motor. Thus frequency sensor 107C, which is adapted to measure the frequency of the sound emitted by the drill motor can thus be used to give an indication of the density and softness of the tissue being drilled.

The measurement of the vibration of the tissue when drilled or otherwise worked by the surgical tool can provide an additional means of detecting tissue characteristics. Different tissues emit sounds having different frequencies, as the vibrations generated by the drilling are different for drilling through different materials. Perhaps even more useful is that such sounds can give an indication of tissue thickness, since the thicker the material being drilled, sawed or contacted, the lower the frequency of the sound generated by the contact of the surgical tool with the tissue. Thus, not only could a sound sensor 107E give an indication of the tissue type being drilled, but the pitch detected by a sensor for a given material may also indicate where the surgical tool is positioned in that tissue. For instance, as the tool tip approaches the edge of the bone, even before it breaks through, the sound emitted is expected to undergo an increase in pitch.

In some implementations, the system uses sensor output to enable the insertion of pedicle screws to a greater depth than predicted by the operative plan. The sensors may detect that, contrary to the expected situation from the preoperative surgical plan, the tool is not yet approaching a forbidden region, and that additional bone is available for advance of the tool. This allows further penetration of the tool, and use of the full available expanse of the bone, expanding the utility and accuracy of the original surgical plan.

Electrical impedance is a property of the tissue and is different in cortical bone compared to cancellous bone, and in bone compared to a fluid-filled or empty space such as the spinal canal, or in cortical bone compared to muscle. Every tissue has different electrical impedance determined by its composition. Some materials have high electrical impedance while others have low electrical impedance. Therefore, measuring the tissue impedance at the site of the drill tip via electrodes 107F positioned in the tissue, can be used to determine the type of tissue, and in some cases, the position of the drill within the tissue.

Except for the last mentioned impedance sensor, each of these parameters is affected by operation of the saw or drill, and the signal changes as the tool progresses from one tissue type to another. The ideal parameter is one that begins to change before the saw or drill reaches the edge of the bone or other danger zone, or issues a warning of impending hazard, before the drill bit transitions from one tissue to another. Each of these parameters is discussed in more detail hereinbelow.

Whereas not all sensors are used for every system or in every surgical procedure, the output of the sensor or sensors 107A-107F employed is input into a control system 101, which analyzes the output signal of each sensor being monitored. The controller is additionally supplied with anticipated values of the specific parameters for the anatomical structure in which the controller calculates or estimates that the surgical tool 105 is operating, according to the surgical plan. These anticipated sensor output values may be stored in a database which the controller 101 is able to access. Should the controller receive sensor outputs which vary more than a predetermined amount from those expected, the controller may provide a signal to the robotically controlled arm 104 to either slow the speed of tool advance, shut off the power to the tool, temporarily halt the motion progress of the tool, or change the tool trajectory to avoid damage to surrounding tissue. Additionally or alternatively, the controller may issue a warning to a human operator.

A safety mechanism using a combination of some or all of the above mentioned controller responses may have good potential to prevent collateral damage. The system may be configured to allow the use of any single parameter to provide a warning signal to the human operator, to change the tool's speed or trajectory, or to disconnect power to the surgical tool. The selected one or more controller safety responses may be chosen by the system, based on the given tool, surgical procedure, or patient characteristics. This flexibility provides the greatest safety margin by personalizing the approach to the given situation. Preferably, the system may be configured to use a combination of sensor outputs, in accordance with both intrinsic properties of the surgical tool and tissue properties, as well as comparing actual distance and angle measurements intraoperatively to the corresponding measurements taken from the preoperative imaging studies, to provide a higher level of safety to the drilling process.

In alternative embodiments, the controller does not use a database of expected sensor outputs to determine whether the surgical tool is approaching forbidden regions; rather, detection of a sudden increase or decrease in the intensity of a sensor output, is an indication that the surgical tool is transitioning, or has already transitioned, between tissues prompts the controller to take one of the actions described above.

Drilling of a pedicle screw hole is used as an example of the criticality and need of the presently disclosed system. Because the vertebral pedicle is a narrow bridge of bone between the vertebral body and the spinous processes, the accuracy required for aligning the drill is very high, and a small error may have serious results. Especially for a robotically performed procedure, the system needs to be configured with added layers of safety, beyond the instructions to the robot by the surgical plan based on preoperative three-dimensional images. The system has to provide the sensory feedback that a human operator would feel, and being robotic, can provide even further safety mechanisms to prevent inadvertent damage to either the neural tissue within the spinal canal, the paraspinal muscles on the exterior of the vertebrae, or peripheral nerves and blood vessels.

If or when the system senses, through any of the system sensor outputs 107A-F, that the saw, drill, or milling tool is close to impinging on a forbidden area, or if the sensors imply from the sensor-detected type of tissue in which the tool is operating, that the tool has deviated more than a certain amount from the planned trajectory, the system may employ a number of options for averting tissue damage or preventing the tool from entering a region where it is not allowed.

The solutions proposed apply to the most common methods of surgical bone cutting and milling, which use either a conventional drill or saw, or a high-power ultrasound surgical blade. Different sensors may be used for different surgical procedures, and the type of sensor used may be tailored to the surgical procedure. For drilling applications, where conventional mechanical rotary action may be used, some of the expected sensor output parameters may differ from those used in ultrasound cutting procedures.

Figure 2A:
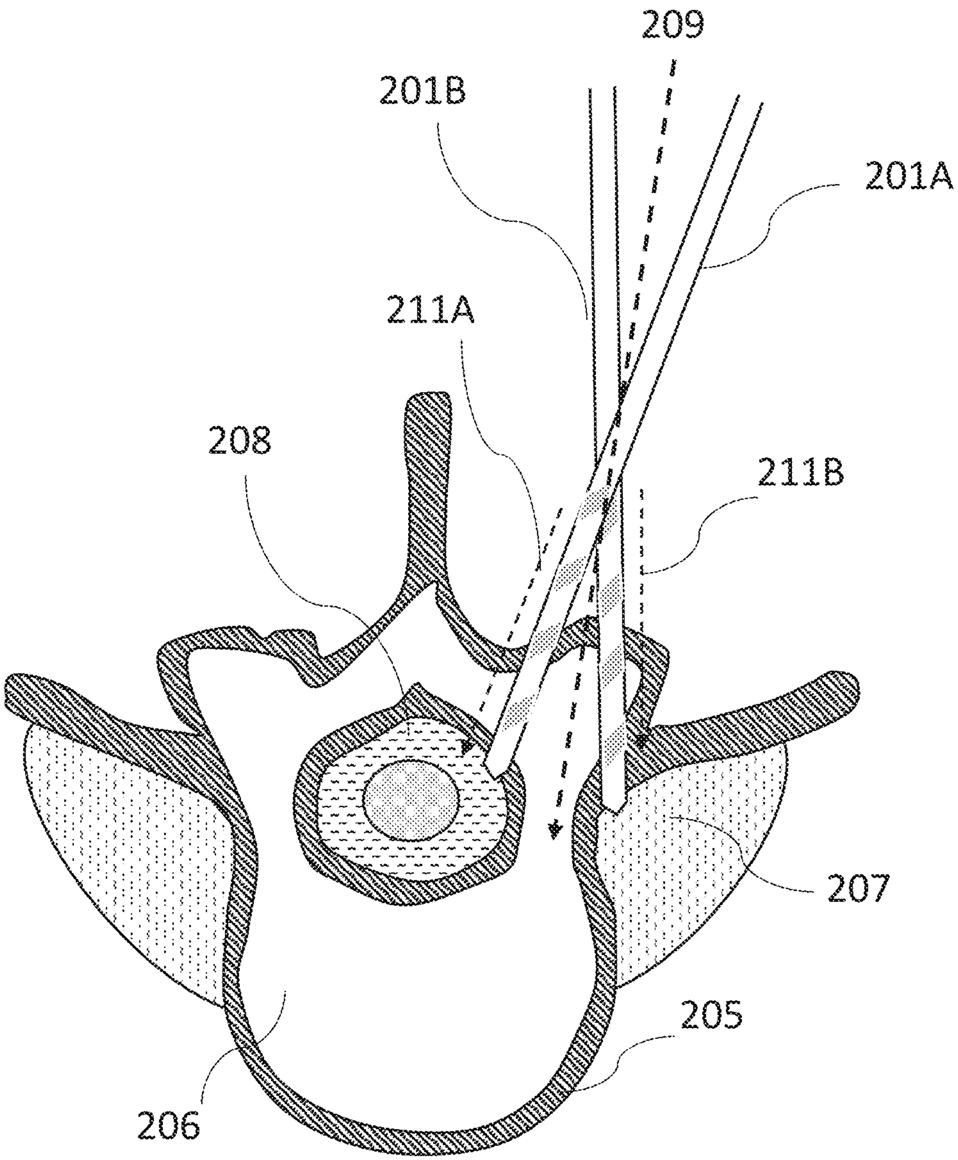
FIGS. 2A to 2D illustrate operation of the safety mechanism by measurement of various sensed outputs related to a surgical drill in operation.

Reference is now made to FIGS. 2A-2D, illustrating how the safety mechanisms described in FIG. 1 are designed to protect the patient's tissue from damage, by giving an indication as to whether the surgical plan is being followed as intended. In FIG. 2A, there is shown the example of a surgical tool intended to follow the trajectory 209, delineated in a surgical plan, which in the exemplary illustration of FIG. 2A, is a trajectory traversing the spinal lamina and pedicle into the vertebral body 206. On the right side of the vertebra shown in FIG. 2A are two examples of unintended trajectories which the surgical tool may take, should the coordinate system of the surgical tool tip be incorrectly aligned with a map of the patient's anatomy. Drill bit 201A follows trajectory 211A, entering the vertebra at an angle medial to the pedicle, leading to the penetration of the drill bit into the spinal canal 208. Drill bit 201B follows trajectory 211B leading to entry of the drill into the adjacent paraspinal muscles 207. Given the small differences in the angle of the surgical tool between a correct trajectory 209 as compared with an incorrect trajectory 201A, 201B, safety mechanisms are required to ensure proper insertion of the tool.

Figure 2B:
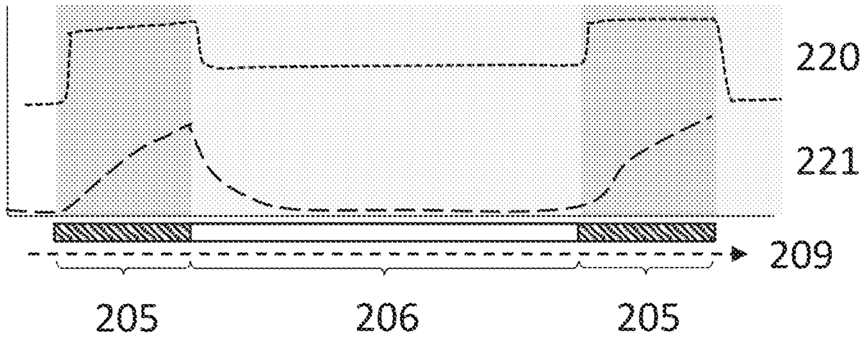

Reference is now made to FIG. 2B, showing changes in measured parameters as the drill bit advances through the vertebra along the correct trajectory 209, represented along the x-axis, as cortical bone 205, cancellous bone 206, and if the path continued, again through cortical bone 205. Two exemplary parameters are measured, represented by traces 220 and 221, their individual relative intensity being shown on the y-axis. These parameters are for illustration purposes only, and may be any of the parameters discussed in FIG. 1 above, that change as the drill passes through various anatomical structures. The intensities of the sensor output traces are marked on the ordinate of the graph, such that the exemplary graph of FIG. 2B shows how the intensity of sensor outputs are affected over trajectory 209 illustrated on the x axis.

Trace 220 shows the sensor output that would be obtained by, for instance, the sound level or vibration of the drill, or the power drawn, as it proceeds along trajectory 209. The sensor output rises sharply as the drill tip enters the cortical bone, and slightly more as the drill proceeds through the cortical bone thickness, because of the increased friction on the rotating drill, falling as the cancellous bone is encountered, and rising again in the opposite layer of cortical bone. This behavior is what would be expected from a rotary drill, while an ultrasound cutting tool would behave slightly differently. Trace 221 in FIG. 2A illustrates another representative parameter that increases more gradually as the drill enters the bone, but has a sharper decrease when the drill exits the bone. Each parameter may follow a different and unique curve, some showing an opposite path to others, such as a decrease upon entry into bone. Each of these parameters change as the drill, if allowed to, passes through the anatomical structures 205 and 206, and 205 again. In a typical implementation, a control system receives sensor outputs such as 220 and 221, and analyzes the output signals. A sudden increase or decrease in any of these parameter values 220 and 221, may indicate to the controller that the drill has passed a tissue boundary or interface, and the controller should use its preprogrammed routine to determine what action, if any, to take.

The controller may additionally be supplied with anticipated values expected of the sensor outputs, for the part of the anatomical structure of the patient in which the controller calculates the surgical tool to be operating. These anticipated sensor output values may be stored in a database to which the controller has access. The anticipated thresholds of each tissue parameter may differ based on a given patient's bone density, age, gender, skeletomuscular condition, osteoporosis measured by z-score, and any concomitant diseases that may affect the safety threshold of a measured parameter. Additionally, the sensor outputs anticipated for different tissues may differ depending on the angle of the surgical tool 105, the entry rate of the surgical tool 105, and the depth of the surgical tool 105 within the tissue, or from the skin, of the patient. The actual sensor outputs can thus provide a reflection of the tool's movement and therefore of its spatial location relative to or within a given tissue. Algorithms and methods of artificial intelligence, such as deep learning and machine learning, may be used to analyze this information over space and time to develop an accurate map of expected sensor outputs for a particular tool in a given tissue.

One such way that the system may use artificial intelligence and/or machine learning to fine-tune the sensor feedback system, is to utilize sensor outputs of experimental studies or actual previous surgical procedures, to analyze how sensor outputs are affected as different surgical tools traverse different tissues. The system can thus learn to recognize specific patterns and behaviors of the sensor response outputs as the tool traverses a given anatomical structure. For example, a decrease in, for instance, the sound intensity and vibration and possibly the frequency emitted by the surgical process, in combination with a decrease in the power and force required to traverse a given bony feature, can be used to provide an indication that the tool is transitioning, or has already transitioned, from cortical bone to cancellous bone. As is illustrated in the exemplary FIG. 2B, a decrease of, for instance, the vibration intensity of the drill 201B, as well as the force exerted by the drill, occurs as the drill passes from cortical bone 205 to cancellous bone 206. Once the drill has transitioned to moving through cancellous bone 206, there is an overall drop in, for instance, both the vibration of the drill, and the force exerted by the drill. This analysis and other relevant clinical information can be inputted into the database, and/or stored as a data set, with different sensor output patterns labelled as indicating different tissues, to assist in defining the expected parameter measurements as the tool traverses a given anatomical feature. Thus, the specificity of the measurements allows a greater definition of the expected measurements for a given parameter at a given depth or position of a specific tool operating on a specific anatomical feature, such as a vertebra.

A further advantage of the use of a database of anticipated sensor output values may be the ability of artificial intelligence to distinguish finer differences in sensor output behavior as the tool operates in and passes between types of soft tissues, such as muscle, ligament, and loose connective tissue. The system may further employ edge learning by touching the tool to different tissues, to learn the properties of each tissue in that particular patient. Such techniques especially apply for ultrasonic powered tools.

Additionally and alternatively, artificial intelligence analysis of stored data may be used during the surgical procedure to provide the system or the surgeon with positional information based on measured parameters. During the operation itself, the system may incorporate real time measurements of parameters that define the tool position in relationship to other tissue features. This segmental tracking provides an additional source of information related to tool position in the tissues, and may be integrated with the changing parameters to enhance the accuracy of the safety mechanism.

Figure 2C:
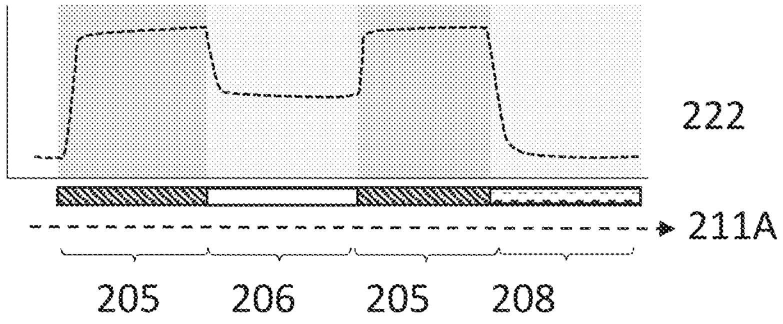
Figure 2D:
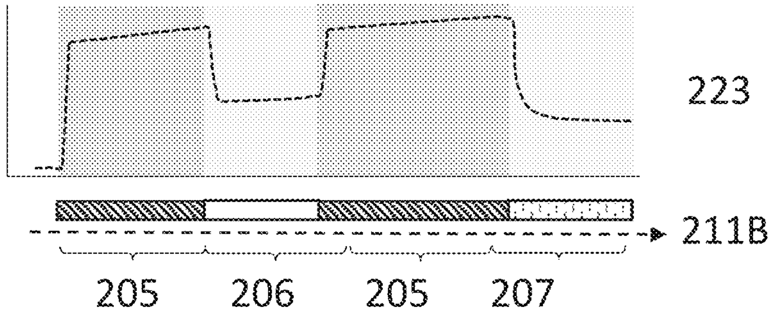

In FIG. 2C, an exemplary power trace 222C is shown as the drill bit proceeds along trajectory 211A through cortical bone 205, cancellous bone 206, again through cortical bone 205, and eventually, if not stopped, into the spinal canal 208. In FIG. 2D, the trace 223 for another incorrect trajectory 211B is shown, except that the drill enters the muscle tissue 207, which has a relatively greater density that the potential space of the spinal canal 208, this greater density being discernible as a different level of the measured parameter of curve 223 in region 207, as compared to region 208 of FIG. 2C. These examples are for illustration only, as activation of the safety mechanism is designed to prevent the drill bit from penetrating beyond the second section of cortical bone. Use of a combination of parameters form a combination of sensors provides a greater level of safety compared with the measurement of a single parameter.

Figure 3A:
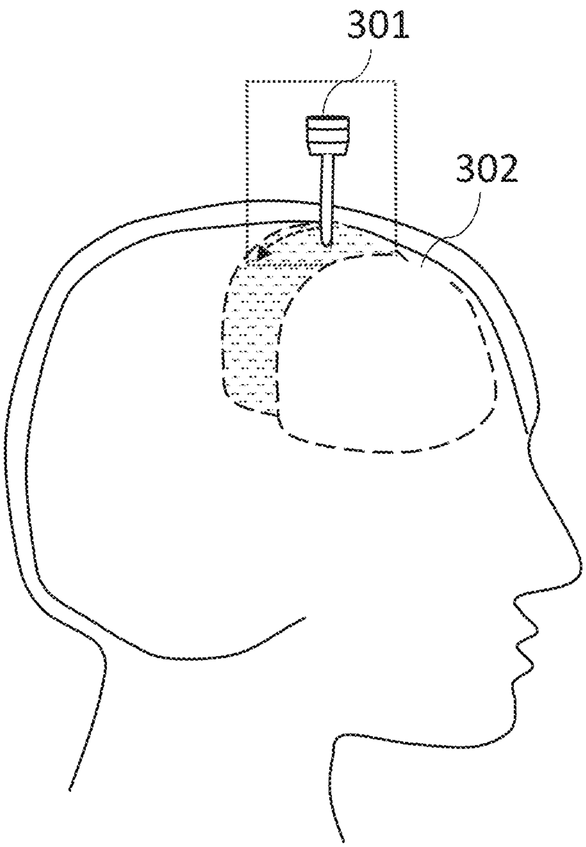
FIGS. 3A and 3B schematize the use of an ultrasonic bone cutting blade for a cranial incision.
Figure 3B:
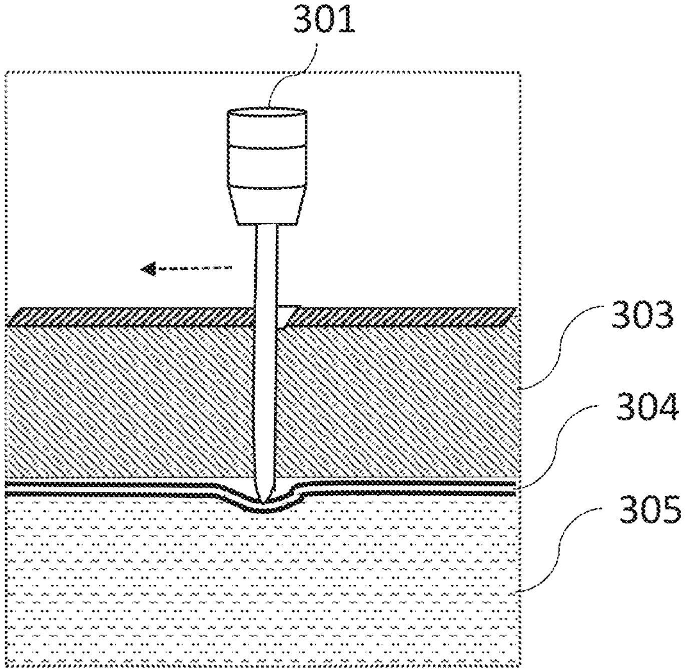

Reference is now made to FIGS. 3A and 3B, illustrating another exemplary implementation of the disclosed methods, which provides a safety mechanism for an ultrasonic bone cutter being used in a cranial procedure. In FIG. 3A, the bone cutter 301 is used to create a bone flap 302 in the skull. Ultrasonic cutting of bone is accomplished by amplifying and converting an electrical signal into ultrasonic vibration of a blunt blade at a frequency of the order of several tens of kHz, 22,500 kHz being one commonly used frequency; the recurring impacts pulverize the crystalline bone structure, whereas the more compliant, adjacent soft tissue is less affected by the ultrasonic oscillation. Referring to FIG. 3B, due to the different tissue densities between bone 303 and the underlying meninges 304 covering the neural tissue 305, the ultrasound cutter may depress the dural meninges if contacted thereto, but does not penetrate it under normal operating conditions. Such an ultrasonically powered cutting tool is thus especially useful for operating in bone in the vicinity of neural tissues, such as the tool used to cut the skull in the case of FIGS. 3A and 3B, or to create an osteotomy in a vertebra in an operation where preservation of underlying neural tissue is essential. However, this method may result in thermal damage and tearing of the meninges; thus, additional safety mechanisms are required to prevent tissue damage.

With robotic control of the operation based on preoperative three-dimensional images, the ultrasonic blade can be inserted precisely to the depth of the vertebra, skull, or other bone to be cut in any given location. However, even though prior registration may be performed between the position of the surgical tool 301 and the anatomy of the patient, small anatomical shifts in the tissue planes relative to the surface may introduce small but significant changes in the actual position of the tool. Therefore, the additional safeguards and information supplied by the various sensor embodiments of the present application, are of great importance in assisting in ensuring safe operating procedures.

Figure 4:
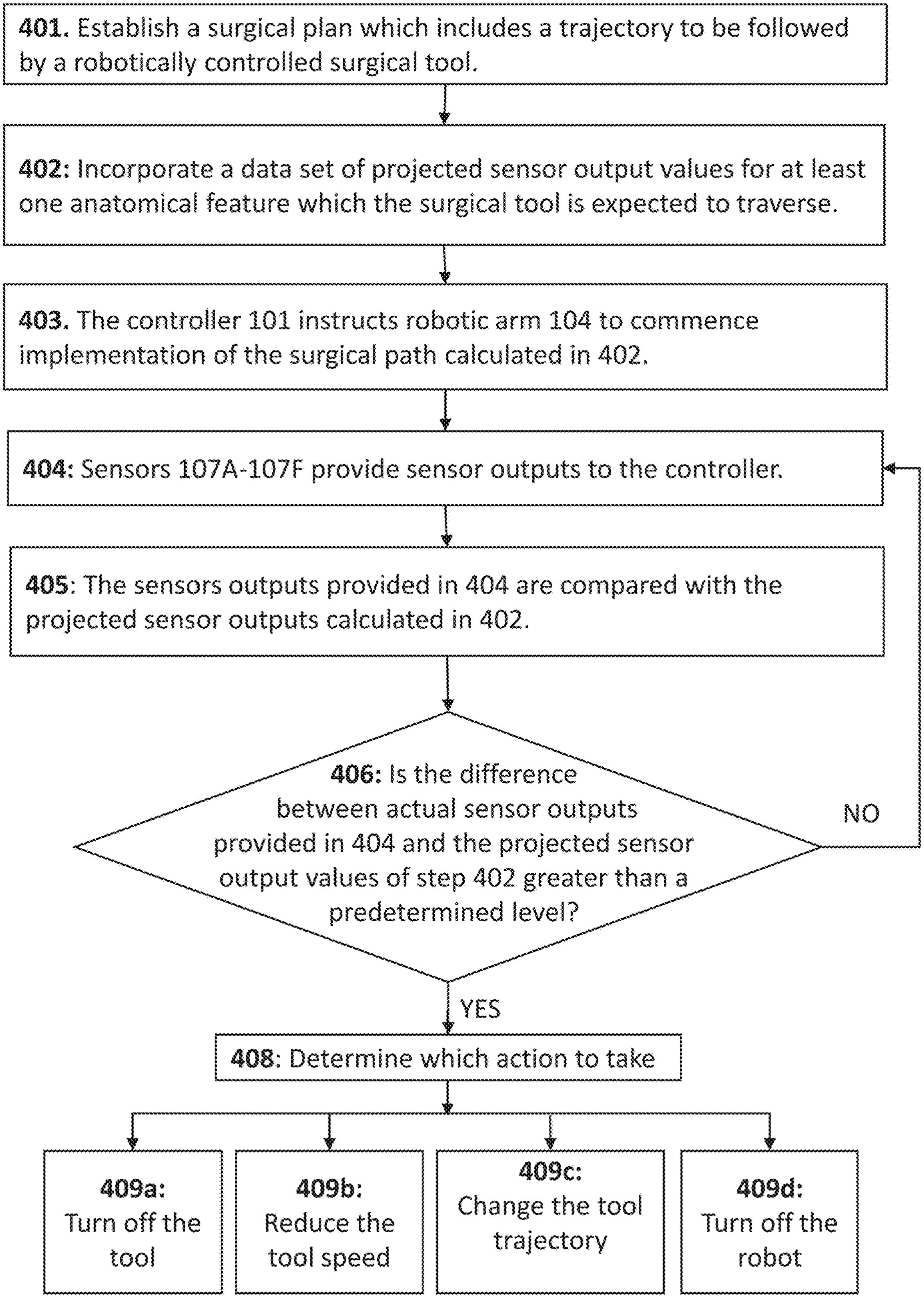
FIGS. 4 and 5 are flow charts outlining the steps performed in two alternative illustrative implementations of the methods which may be used with the system of FIG. 1.

Reference is now made to FIG. 4, which shows a flow chart illustrating the steps involved in an implementation of an exemplary method which could be used with the system of FIG. 1. In step 401, an operative plan is established, defining a path for a robotic arm 104 to direct a surgical tool 105 along a planned trajectory. In step 402, using knowledge of the interaction of the tool with various types of tissue, and knowledge of the path to be followed, the expected changes in tissue density that the tool is expected to experience along the path defined in step 401, are determined. In step 403, the robotic controller 101 provides guidance to the robotic arm 104 which operates a surgical tool 105. In step 404, interaction of the tool 105 with the various tissues through which the tool passes generates outputs from at least some of the sensors 107A-107F, and these outputs are input into the controller 101. The sensor outputs are related to tool operation, such that they provide information regarding the type of tissue through which the tool is moving. In step 405, the system analyzes these outputs of the sensors relative to the anticipated sensor outputs expected from step 402. This analysis could be a simple comparison between the actual sensor values measured by sensors 107A-107F as compared with the sensor outputs anticipated for the given tissue which the system calculated that the surgical tool 105 is traversing. However, the system may additionally employ artificial intelligence to give an indication of whether the tissue being operated on has the tissue properties expected, by analyzing patterns and behaviors of the changes in sensor outputs, as the process progresses, as was described in FIG. 2B. In step 406 of the exemplary procedure illustrated, the system determines, using the result of the analysis performed in step 405, whether the tool trajectory has veered from the planned path, for instance because of tissue motion, and from the history of the trajectory, whether that deviation is more than an allowable distance, or whether the tool has entered a tissue of a region where the tool is forbidden to operate, or whether the system has determined from specific sensor outputs that the tool is about to enter a forbidden region. If no such diversion from the surgical plan is found, the sensors 107A-107F continue in step 404, to measure the parameter(s) of interest as the operation proceeds according to the operative plan.

If, on the other hand, a deviation from the surgical plan is found, then in step 408 the system determines which action to take. The system may have inbuilt default responses, such that if any, or if a combination of sensor output values exceed predetermined thresholds, the system responds. Alternatively, the system may run an algorithm that may incorporate machine learning, deep learning, or other technique of artificial intelligence, to determine which action to take. The decision may be based on the specific sensor outputs received by the control system, and the analysis performed in step 405. The system may respond using any one of the following steps:

(viii) Step 409*a*: turning off power to the tool.

(ix) Step 409*b*: reducing the speed of drill rotation, frequency of ultrasound vibration, or other aspect of tool operation.

(x) Step 409*c*: changing the trajectory of the tool 105 via robotic control 104.

(xi) Step 409*d*: turning off the robot.

In addition, in any of the steps, a warning may be issued to the operator.

Figure 5:
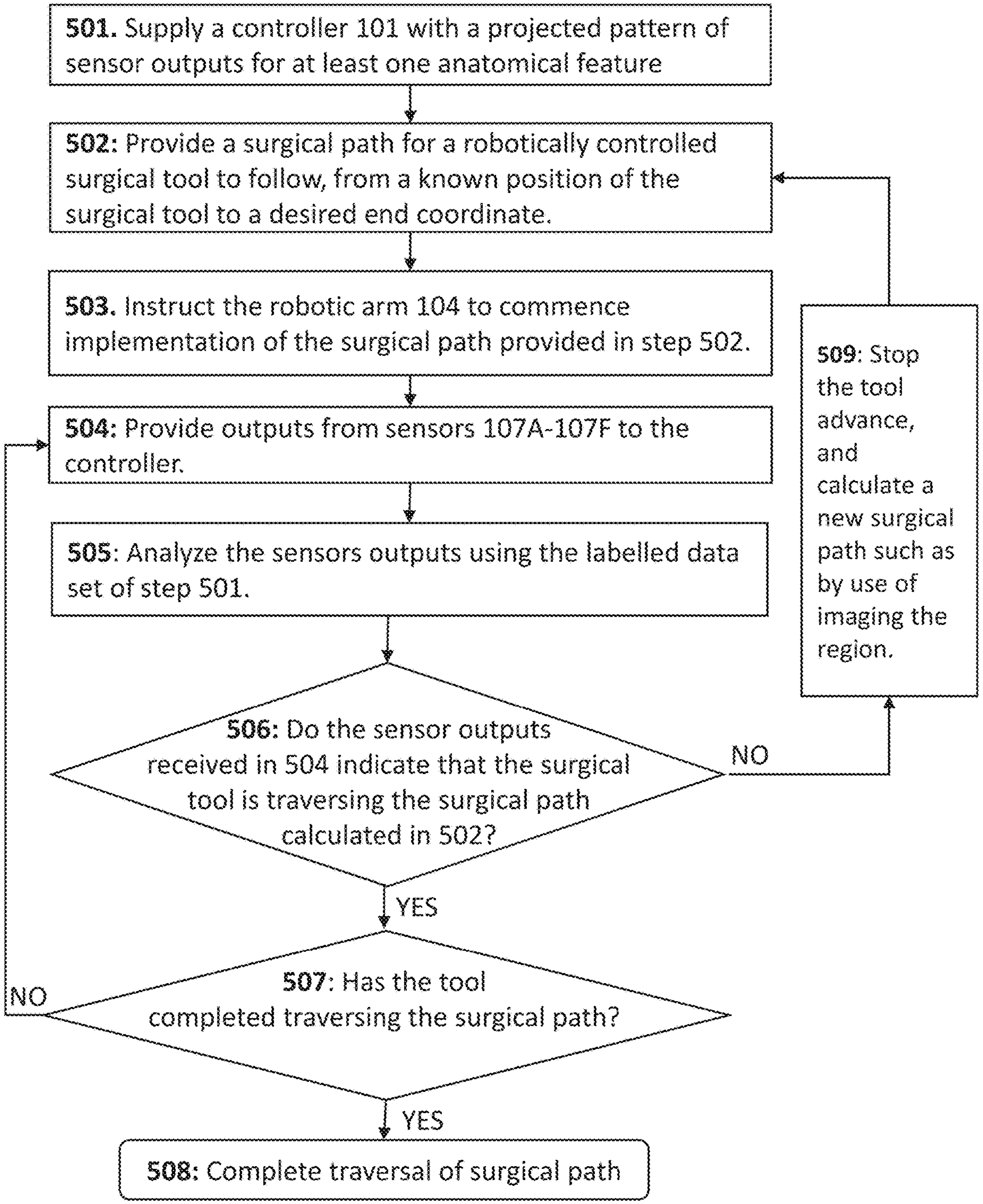

Reference is now made to FIG. 5, a flow chart illustrating the steps involved in an alternate exemplary implementation of methods relating to the system of FIG. 1. In step 501, the controller is supplied with data regarding the projected patterns of sensor outputs for various sensors reacting with various anatomical features. This data could come from a known external database, or from a database derived from previously executed experimentation to obtain the expected responses from the particular surgical tool set-up used in the robotic system being used. In step 502 a planned surgical path is provided for the robotically controlled surgical tool to follow, from a known starting position of the surgical tool to a desired end target position. In step 503, the robotic controller 101 instructs the robotic arm 104 to commence implementation of the surgical path of 502. In step 504, the sensors 107A-107F provide outputs to the controller as the surgical path is implemented. In step 505, the controller analyzes the sensors outputs using the labelled data of step 501. In step 506 of the exemplary procedure illustrated, the system determines, using the result of the analysis performed in step 505, whether the sensor outputs received by the controller in 504 indicate that the surgical tool is traversing the surgical path decided upon in step 502. If the tool is following the planned path to within a predetermined deviation limit, then in step 507 the system determines if the tool has completed traversing the surgical path, and if so, then in step 508 the method ends. On the other hand, if in step 506, it is determined that the tool is not on the intended path, then in step 509 the system aborts the present path of the surgical tool, and returns to step 502 to recalculate the tool position and a new surgical path, and recommences its implementation.

If it is determined that the deviation from the intended path is due to a shift of tissue in the region of the surgery, the controller may issue an instruction to perform intraoperative imaging to determine the current tissue dispositions before planning a new surgical path and then either continuing from the point at which the original path was stopped along an amended path, taking into account the tissue shift, or recommencing the implementation of a new surgical path.

Figure 6:
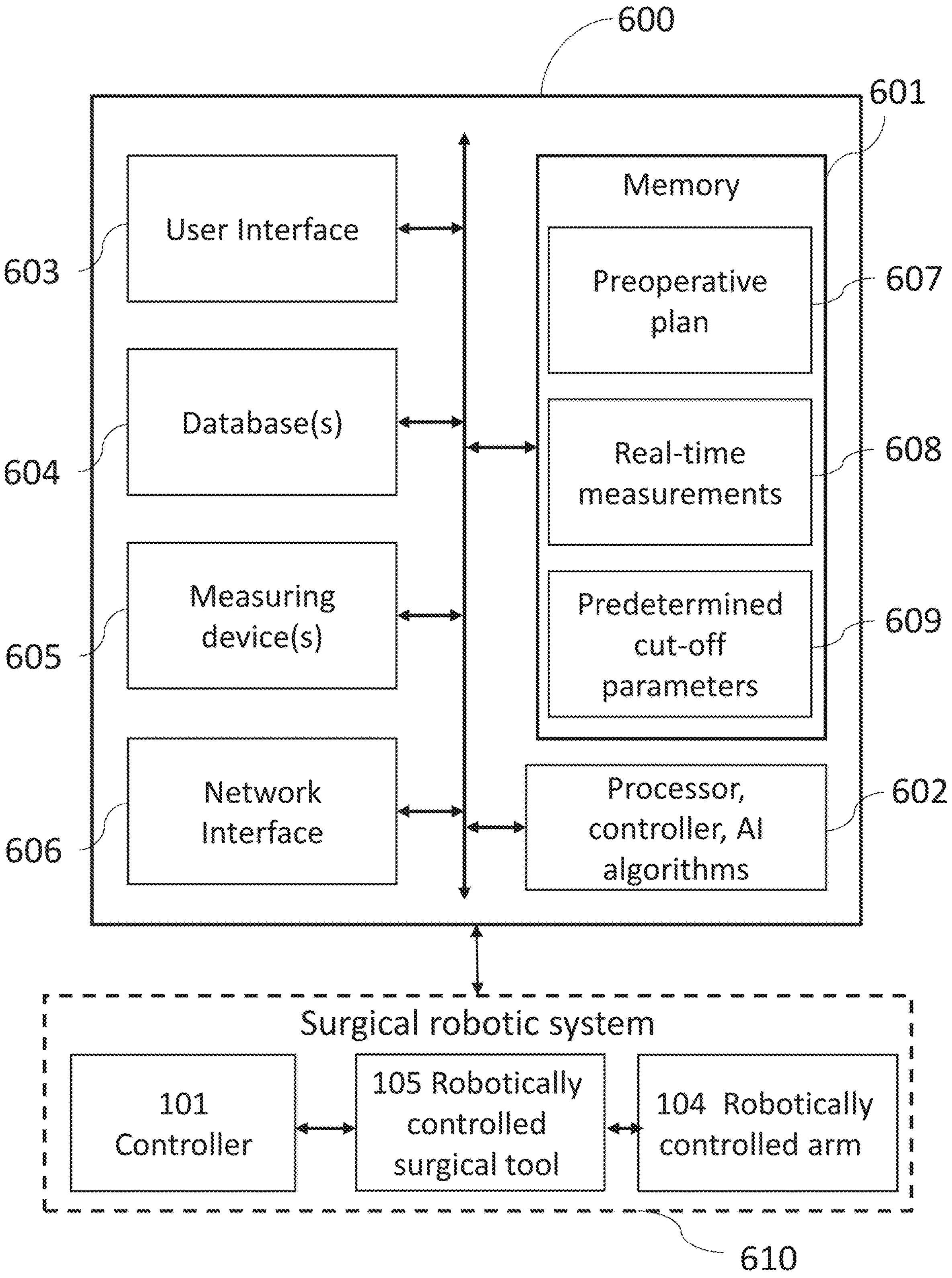
FIG. 6 schematizes the structural components of an exemplary block diagram of a controller incorporated into the system used to implement the safety mechanism.

Reference is now made to FIG. 6, schematizing the components of an illustrative system for carrying out a representative implementation of the disclosed methods. The control system 600 comprises a memory unit 601, a processor 602, a user interface 603, one or more databases 504, one or more measuring devices 605, and a network interface 606. The memory (RAM) 501 is used to store at least some of: (i) a preoperative plan 607, (ii) real-time measurements 608 obtained by the measuring devices 605, and (iii) predetermined cut-off values for the measured parameters 609. The processor 602 comprises a controller for executing optional algorithms for artificial intelligence such as machine learning and deep learning. The system 600 is in communication with a surgical robotic system 610 comprising components shown schematically in FIG. 1, including a controller 101 that operates at least one robotically controlled arm 104 holding and controlling a surgical tool 105.

In this disclosure, the term system may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components, such as optical, magnetic, or solid state drives, that provide the described functionality; or a combination of some or all of the above, such as in a system-on-chip. The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this disclosure may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A method for monitoring progress of a robotically directed surgical tool along a predetermined path through different tissues, the method comprising:

determining from a known position of the surgical tool along the predetermined path, a tissue which the surgical tool is expected to be traversing;

detecting at least one sensor output arising from interaction of the surgical tool with the tissue which the surgical tool is traversing;

comparing the at least one sensor output with expected sensor output from the interaction of the surgical tool with the tissue which the surgical tool is expected to be traversing; and determining that the surgical tool is departing from the predetermined path if the comparison shows that the at least one sensor output is meaningfully different from the expected sensor output.

2. The method according to claim 1, wherein the at least one sensor output is indicative of at least one of:

(i) a sound emitted by a surgical process;

(ii) electrical power drawn by the surgical tool or by a robot directing the surgical tool;

(iii) a sound emitted by a motor of the surgical tool during its progress;

(iv) mechanical force which the surgical tool experiences by reaction of the surgical tool with the tissue;

(v) mechanical vibrations which the surgical tool undergoes as the surgical tool proceeds through the tissue; or (vi) electrical impedance of the tissue which the tool is traversing.

3. The method according to claim 2, wherein if the surgical tool is found to be departing from the predetermined path, performing at least one of:

(i) halting motion of the surgical tool along a planned trajectory;

(ii) reducing advance speed of the surgical tool;

(iii) reducing machining ability of the surgical tool;

(iv) turning off power to the surgical tool; or (v) issuing a warning to an operator of a system.

4. The method according to claim 1, wherein the predetermined path through different tissues includes a procedure in a bone tissue, and wherein the surgical tool is determined to depart from the predetermined path upon passage of the surgical tool out of the bone tissue.

5. The method according to claim 1, further comprising using artificial intelligence to analyze whether the at least one sensor output is falling outside of a predetermined normal range from the expected sensor output.

6. The method according to claim 1, wherein if it is determined that the surgical tool is departing from the predetermined path, performing at least one of: disabling power to the surgical tool, decreasing power to the surgical tool, or changing a trajectory of the surgical tool.

* * * * *